United States Patent [19]

Murtiashaw

[11] Patent Number: 5,134,225

[45] Date of Patent: Jul. 28, 1992

[54] PROCESSES AND INTERMEDIATES FOR N-(S-3-ALKYL-HEPTANOYL)-D-GAMMA-GLUTAMYL-D-ALANINE

[75] Inventor: Charles W. Murtiashaw, North Stonington, Conn.

[73] Assignee: Pfizer Inc., New York, N.Y.

[21] Appl. No.: 346,118

[22] Filed: Feb. 21, 1989

[51] Int. Cl.$^5$ .............................. C07K 1/10; C07K 5/08
[52] U.S. Cl. ................................. 530/331; 530/333; 530/338
[58] Field of Search ....................... 530/333, 331, 338

[56] References Cited

U.S. PATENT DOCUMENTS

| | | | |
|---|---|---|---|
| 3,985,722 | 10/1976 | Yoshida et al. | 260/112 R |
| 4,045,475 | 8/1977 | Chan et al. | 260/488 |
| 4,113,968 | 9/1978 | Mori et al. | 560/124 |
| 4,374,264 | 2/1983 | McGarry | 560/205 |
| 4,401,658 | 8/1983 | Bouchaudon et al. | 424/177 |
| 4,565,653 | 1/1986 | Ives et al. | 260/112.5 R |
| 4,767,743 | 8/1988 | Rizzi | 514/18 |

OTHER PUBLICATIONS

Morrison et al. *Organic Chemistry*. 1959, p. 126.
Paulson et al. *Organic Chemistry*. 1980, pp. 1025–1031.
Herberman et al., eds. *13th International Congress of Chemotherapy*. 1983. pp. 203/19–203/35.
Basic Principles of Organic Chemistry, John D. Roberts et al., p. xiii, (1964).
Greenwood, J. Org. Chem., v. 27, pp. 2308–2311, (1962).
Carruthers, "Some Modern Methods of Organic Synthesis", 2nd ed., Cambridge University Press, Cambridge, pp. 106–107, 340–341 (1978).
House, "Modern Synthetic Reactions", 2nd ed., Benjamin, Inc., Menlo Park, CA, pp. 263, 269, 274, 275 (1972).
Chemical Abstracts, v. 101, abstract 6924e; abstracting Vig et al., Indian J. Chem., Sect. B, v. 22B, pp. 1126–1128 (1983).
Katsuki et al. J. Am. Chem. Soc., v. 102, pp. 5974–5976 (1980).
Sharpless et al., Pure Appl. Chem., v. 55, pp. 589–604 (1983).
Midland et al., J. Org. Chem, v. 50, pp. 1143–1144 (1985).
Midland et al., Tetrahedron, v. 40, pp. 1371–1380 (1984).
Kondo et al., in ACS Symposium Series-Synthetic Pyrethroids (1976), pp. 128–136.
Crombie et al., J. Chem. Soc., pp. 869–875 (1952).

*Primary Examiner*—Howard E. Schain
*Attorney, Agent, or Firm*—Peter C. Richardson; J. Trevor Lumb; Mervin E. Brokke

[57] ABSTRACT

Immunoregulatory N-(S-3-alkyl-4-heptenoyl)- and N-(S-3-alkylheptanoyl)-D-gamma-glutamyl-glycyl-D-alanine and esters thereof are synthesized via R-trans-2-hexen-4-ols, R-3-alkyl-4-heptenoic acid and S-3-alkylheptanoic acid.

8 Claims, No Drawings

PROCESSES AND INTERMEDIATES FOR N-(S-3-ALKYL-HEPTANOYL)-D-GAMMA-GLUTAMYL-D-ALANINE

The present invention is directed to an advantageous process for immunoregulatory agent of the formula

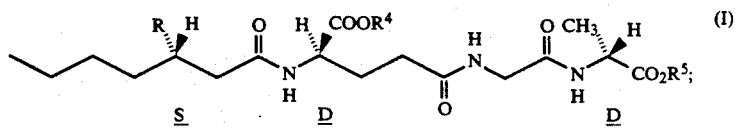

wherein R is methyl or ethyl; and $R^4$ and $R^5$ are each hydrogen, or one of $R^4$ and $R^5$ is hydrogen and the other is $(C_1-C_6)$alkyl or $(C_6-C_8)$ cycloalkylmethyl; to a process and intermediates for the manufacture of trans-R-3-alkyl-4-heptenoic acids (VIb, below) and S-3-alkyl-heptanoic acids, the latter of the absolute stereochemical formula

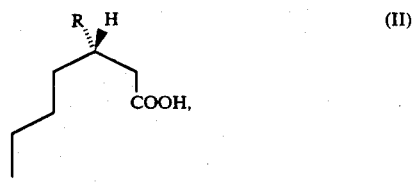

where R is defined above, having utility as intermediates in the synthesis of the compound of the formula (I); and to immunoregulatory agents (or precursors) of the absolute stereochemical formula

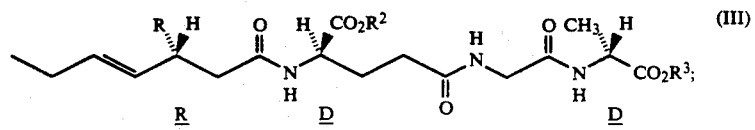

where R is as defined above and $R^2$ and $R^3$ are both hydrogen (IIIa) or a pharmaceutically acceptable salt thereof or $R^2$ and $R^3$ are each independently $(C_1-C_6)$alkyl, $(C_6-C_8)$cycloalkylmethyl or benzyl (IIIb).

Optically pure S-3-methylheptanoic acid (II, R=CH$_3$) was originally prepared from the corresponding racemate in unspecified yield by multiple crystallizations of the quinine salt at $-15°$ C. [Levene et al., J. Biol. Chem., 95, pp. 1-24, 1932, at page 18, there called 2-n-butylbutyric acid-4]. Optically active 3-methylheptanoic acid has subsequently been produced by a number of other methods (Soai et al., J. Chem. Soc., Chem. Commun. 1985, pp. 469-470; Oppolzer et al., Helv. Chim. Acta. 68, pp. 212-215 (1985); Ohno et al., U.S. Pat. No. 4,564,620 (1986); Mori et al., Synthesis 1982, pp. 752-753; Oppolzer et al., Helv. Chim. Acta. 64, pp. 2808-2811 (1981); Mukaiyama et al., Chem. Lett. 1981, pp. 913-916; Posner et al., J. Am. Chem. Soc. 103, pp. 2886-2888 (1981); Mukaiyama et al., Bull. Chem. Soc. Japan, 51, pp. 3368-3372 (1978); Meyers et al., J. Am. Chem. Soc. 98, pp. 2290-2294 (1976)] but these preparations generally suffer from one or more disadvantages (at least 50% of undesired byproduct is carried through to the final stages of the process; the product acid is not optically pure; use of organometallic reagents, difficult to handle on a large scale, is required; overall yields are low; and/or the required reagents are not readily available).

The presently employed asymmetric epoxidation (the so-called Sharpless resolution) has been previously reported (Katsuki and Sharpless, J. Am. Chem. Soc. 102, pp. 5974-5976, 1980; Sharpless et al., Pure Appl. Chem. 55, pp. 589-604, 1983); as has stereospecific Claisen condensation (Chan et al., U.S. Pat. No. 4,045,475).

The relatively new field of immunopharmacology, and particularly that segment thereof which deals with immunomodulation, continues to develop at a rapid pace. A variety of naturally occurring compounds has been investigated, including the tetrapeptide tuftsin, known chemically as $N^2$-[1($N^2$-L-threonyl-L-lysyl)-L-prolyl]-L-arginine. Much attention has been directed to synthetic peptidoglycan derivatives, especially those known as muramyl dipeptides.

The immunoregulatory agents of the formula (I), generally as amorphous lyophilates when $R^4=R^5=H$, and their method of use were earlier disclosed in co-pending PCT Application Serial No. PCT/US85/02351, filed Nov. 25, 1985, a continuation of which is now U.S. Pat. No. 4,767,743. Since that application is not yet publically available, preparation of such compounds and their method of use have been incorporated into the present disclosure in support of utility.

Other immunostimulant peptides have been described in a number of patent specifications:

L-Alanyl-alpha-glutaric acid N-acyl dipeptides in German 3,024,355, published Jan. 15, 1981;

tetra- and penta-peptides containing D-alanyl-L-glutamyl moieties or L-alanyl-D-glutamyl moieties in British 2,053,231, published Feb. 4, 1981 and German 3,024,281, published Jan. 8, 1981, respectively;

N-acyl-alanyl-gamma-D-glutamyl tripeptide derivatives in which the C-terminal amino acid is lysine or diaminopimelic acid in German 3,024,369, published Jan. 15, 1981;

lactoyl tetrapeptides composed of N-lactylalanyl, glutamyl, diaminopimelyl and carboxymethylamino components in EP-11283, published May 23, 1980;

polypeptides having the formula (A)

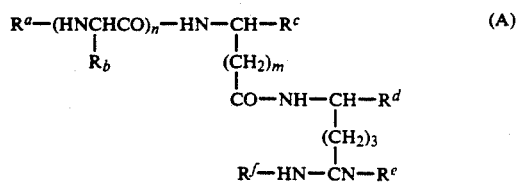

wherein $R^a$ is hydrogen or acyl; $R^b$ is inter alia hydrogen, lower alkyl, hydroxymethyl, benzyl; $R^c$ and $R^d$ are each hydrogen, carboxy, —CONR$^g$R$^h$ wherein R$^g$ is hydrogen, lower alkyl optionally substituted with hydroxy; and R$^h$ is mono- dicarboxy lower alkyl; R$^e$ is hydrogen or carboxy with the proviso that when one of $R^d$ and $R^e$ is hydrogen, the other is carboxy or —CONR$^g$R$^h$; R$^f$ is hydrogen; m is 1 to 3 and n is 0 to 2, and derivatives thereof in which the carboxy and amino groups are protected are disclosed in U.S. Pat. Nos. 4,311,640 and 4,322,341; EP applications 25,482; 50,856; 51,812; 53,388; 55,846 and 57,419; and peptides similar to those of the above formula (A), but wherein $R^4$ forms a basic aminoacid moiety (Ives et al., U.S. Pat. No. 4,565,653; EP application 157,572) or a heterocyclic aminoacid (Ives, EP application 178,845).

Kitaura et al., J. Med. Chem., 25, 335-337 (1982) report $N^2$(gamma-D-glutamyl)-meso-2(L),2(D)-diamino-pimelic acid as the minimal structure capable of eliciting a biological response characteristic of compound of the formula (A) wherein n is 1; $R^a$ is CH$_3$CH(OH)—CO—; $R^b$ is CH$_3$; each of $R^c$ and $R^e$ is —COOH; $R^4$ is —CONHCH$_2$COOH; and R$^f$ is H. Said compound of formula (A) is known as FK-156.

SUMMARY OF THE INVENTION

We have now found efficient processes for the manufacture of intermediates R-3-alkyl-4-heptenoic acids (VIb, below) and S-3-alkylheptanoic acids (II, above) of high optical purity, in excellent overall yield, avoiding organometallic reagents and wasteful by-production of R-enantiomer late in the synthesis. The initial step is a Sharpless type resolution of a trans-4-alken-3-ol of the formula

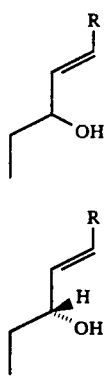

where R is as defined above. Specifically this step involves reacting the racemate of the formula (IV) with t-butyl hydroperoxide, in a reaction inert solvent in the presence of titanium tetraisopropoxide and L-(+)-diisopropyl tartrate, in an amount sufficient to oxidize the S-enantiomer and retain the desired, unreacted R-enantiomer of the absolute stereochemical formula (V).

In the second step, the compound of the formula V is stereospecifically condensed with a tri[(C$_1$-C$_3$)-alkyl-]orthoacetate and, without isolation, the intermediate allyl-enol ether rearranged, in the presence of an acid in a reaction inert solvent, to yield a (C$_1$-C$_3$)alkyl R-3-alkyl-4-heptenoate of the absolute stereochemical formula (VIa).

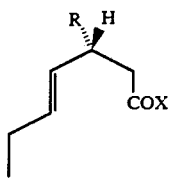

(VIa) X = OR$^1$; R$^1$ = (C$_1$—C$_3$)alkyl (VIb) X = OH (VIc) X = Cl (VId) X = H In one alternative, the ester is then hydrolyzed to a trans-R-3-alkyl-4-heptenoic acid (VIb), and if desired hydrogenated to an S-3-alkylheptanoic acid (II). In another alternative, the ester is first hydrogenated to yield a (C$_1$-C$_3$)alkyl S-3-alkylheptanoate and then hydrolyzed to the acid of the formula (II).

In a further alternative the resolved trans-4-alken-3-ol of the formula (V) is converted to the allyl vinyl ether (IX) by the action of ethyl vinyl ether in the presence of mercuric acetate [Hg(OAc)$_2$] catalyst. The allyl vinyl ether is then rearranged by heating to an R-3-alkyl-4-heptenal, of the formula (VId), which in turn is oxidized, e.g., with Jones reagent (chromic anhydride in dilute mineral acid) to form the above R-3-alkyl-4-heptenoic acid

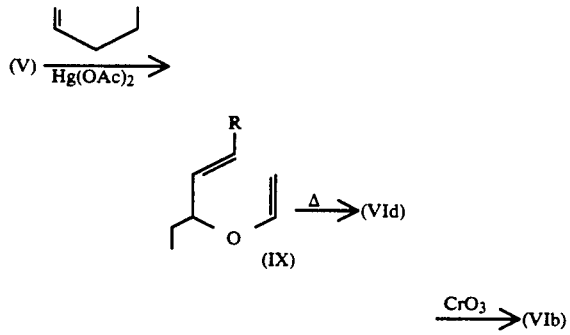

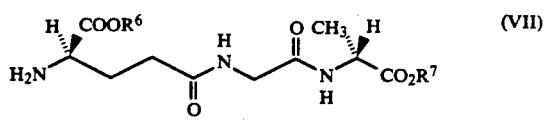

The present invention is also directed to an improved process for the preparation of an immunoregulatory agent of the formula (I) which comprises the steps of (a) coupling an activated form of R-3-alkyl-4-heptenoic acid (e.g., the acid chloride VIc) with a compound of the formula wherein $R^6$ and $R^7$ are both benzyl, or one of $R^6$ and $R^7$ is benzyl and the other is (C$_1$-C$_6$)alkyl or (C$_6$-C$_8$)cycloalkylmethyl, in a reaction inert solvent to form an intermediate compound of the above formula (IIIb) in which $R^2$ and $R^3$ correspond to present $R^6$ and $R^7$; and (b) hydrogenation of said intermediate compound in a reaction inert solvent in the presence of a hydrogenation catalyst, with simultaneous reduction of the double bond and hydrogenolysis of benzyl group or groups.

Finally, the present invention is directed to immunoregulatory agents and/or compound (I) precursors of the formula (III) above. A compound of the formula (IIIa), i.e., $R^2=R^3=$hydrogen, is obtained by conventional ester hydrolysis of a diester compound of the formula (IIIb).

The expression "reaction inert solvent" as employed herein refers to a solvent which does not interact with starting materials, intermediates or products in a manner which adversely affects the yield of the desired product.

The preferred value of $R^1$ is ethyl. The preferred acid catalysts are Lewis acids (e.g., dry HCl, AlCl$_3$). Although the present invention is not so limited, the preferred source of racemic trans-4-hexen-3-ol or trans-4-hepten-3-ol is via reaction of an ethyl Grignard reagent with crotonaldehyde or 2-pentenal, respectively.

DETAILED DESCRIPTION OF THE INVENTION

The present invention is readily carried out. R-trans-4-alken-3-ol (V) is obtained by the technique of asymmetric epoxidation, the so-called Sharpless resolution (references cited above). According to this technique, the undesired S-trans-2-hexen-4-ol in the racemate (IV) is selectively reacted with t-butyl hydroperoxide (at least 0.5 mol, but definitely less than 1 mol per mol of racemic hexenol), in the presence of a molar excess of L-(+)-diisopropyl tartrate and substantially 1 molar equivalent of titanium tetraisopropoxide. The reaction is carried out under anhydrous conditions in a reaction inert solvent such as methylene chloride at reduced temperature, generally in the range of $-20°$ to $-80°$ C. The desired, unreacted R-trans-2-alken-4-ol (V) is isolated by standard methods such as distillation or chromatography. Because of the relatively high volatility of the desired product, low boiling solvents such as pentane and ether are preferred for such chromatography.

The next step is condensation/Claisen rearrangement of the R-trans-4-alken-3-ol (V) and a (C$_1$-C$_3$)trialkyl orthoacetate to yield a (C$_1$-C$_3$)alkyl R-3-alkyl-4-heptenoate (VIa). The reaction can be carried out in a reaction inert solvent, but it is preferable to simply carry out the reaction in excess of the orthoacetate ester, generally at elevated temperature (e.g., at 120°-160° C.). When triethyl orthoacetate (bp 142° C.) is the reagent, reflux temperature is conveniently employed. The reaction is carried out in the presence of an acid catalyst. Acids such as propionic acid, pivalic acid, 2,4-dinitrophenol, dry HCl and AlCl$_3$ are effective. The preferred catalysts are Lewis acids. Most preferred is AlCl$_3$.

In one alternative, the resulting ester of the formula (VIa) is hydrolyzed by conventional methods to yield the corresponding unsaturated acid of the formula (VIb).

If desired, the unsaturated acid (VIb), in activated form [e.g., as the acid chloride of the formula (VIc), as a conventional mixed anhydride, or activated by a conventional dehydrative coupling agent such as dicyclohexylcarbodiimide] is coupled in a conventional manner with the compound of the formula

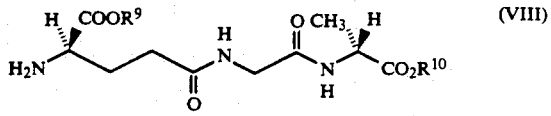

(VIII)

wherein $R^9$ and each independently (C$_1$-C$_6$)alkyl, (C$_6$-C$_8$)cycloalkylmethyl or benzyl, to form an immunoregulatory diester compound of the formula (IIIb). The latter is hydrolyzed by conventional methods to the immunoregulatory diacid compound of the formula (IIIa) or a pharmaceutically acceptable salt thereof.

Alternatively, the compound of the formula (IIIb), when $R^2$ and/or $R^3$ is benzyl, is hydrogenated to form an immunoregulatory compound of the formula (I). In this hydrogenation both the double bond is saturated with hydrogen and benzyl group(s) are hydrogenolyzed. The hydrogenation is carried out in a reaction inert solvent over a hydrogenation catalyst, e.g., nickel or a noble metal; supported (e.g., Raney nickel, Pd/C) or unsupported (e.g. RhCl$_3$). Solvent, temperature and pressure are not critical. Suitable solvents include, but are not restricted to lower alcohols, ethers such as dioxane, tetrahydrofuran or dimethoxyethane, and esters such as ethyl acetate. Preferably ambient temperature is employed, without cooling even if the reaction is somewhat exothermic, avoiding the cost of heating or cooling. Pressure is not critical, but will preferably be below 7 atmospheres in order to avoid expensive, high pressure equipment. Hydrogenation over Pd/C at pressures which are 3-6 times atmospheric pressure is particularly well suited for the present transformations.

Alternatively, the unsaturated acid of the formula (VIb) is hydrogenated under conditions identical to those detailed in the preceding paragraph to yield the S-3-alkylheptanoic acid (II), also obtained from a (C$_1$-C$_3$)alkyl trans-R-3-alkyl-4-heptenoate (VIa) via (C$_1$-C$_3$)alkyl S-3-alkylheptanoate by reversing the hydrogenation/hydrolysis steps. Finally the S-3-alkylheptanoic acid is activated in a manner as detailed above, coupled with a diester of the formula (VII) above, and hydrogenated by methods detailed above to form an immunoregulatory compound of the formula (I) above.

In yet another alternative of the present invention, the R-trans-4-alken-3-ol (V) is converted to the corresponding vinyl ether of the formula (IX), by the action of ethyl vinyl ether in the presence of Hg(OAc)$_2$ as catalyst in a reaction inert solvent (preferably excess of the ethyl vinyl ether) at a temperature in the range of 25°-40° C., conveniently at reflux temperature of the ethyl vinyl ether (bp 36° C.). The resulting vinyl ether (IX) is heated to 140°-200° C., generally in a high boiling, lipophilic, reaction inert solvent such as xylenes or decalin, under pressure if necessary, to stereospecifically rearrange it to the unsaturated aldehyde of the formula (VId). To obtain the unsaturated acid of the formula (VIb), the aldehyde is readily oxidized, conveniently with so-called Jones reagent, an aqueous solution of H$_2$CrO$_4$ formed from CrO$_3$ and a strong acid. Typically, Jones reagent is prepared from an excess of concentrated H$_2$SO$_4$ and CrO$_3$ with about 1:1 by weight of water, then diluted to the desired concentration, e.g., about 3M, with water. To form the unsaturated acid (VIb), the unsaturated aldehyde (VId), generally in solution in a water miscible, reaction inert organic solvent such as acetone is reacted with at least 1 molar equivalent of Jones reagent. Temperature is not critical, e.g., 0°-50° C. is usually satisfactory, with ambient temperature, e.g., 17°-27° C. most convenient.

The crystalline form of the compound of the formula (I) wherein R is methyl and $R^4=R^5=$hydrogen is obtained by crystallization from an organic solvent or a combination of organic solvents. Suitable solvents are acetone, acetonitrile/ethanol and tetrahydrofuran/ether. The preferred solvent in terms of product recovery is acetonitrile/ethanol, but in terms of product purity, acetone is preferred. This novel form has definite stability advantages over the prior amorphous lyophilate. It is much more readily handled, being more dense and much less electrostatic, permitting the preparation of more sophisticated dosage forms.

The pharmaceutically acceptable mono- and dibasic salts of the compound of the formula (I) or (IIIa) are generally obtained by treating a solution, preferably an aqueous solution of the acid with a base such as NaOH, KOH, $Na_2CO_3$ or an amine, in the appropriate stoichiometric proportions. The salts are isolated by evaporation or by precipitation.

The products of this invention of the formula (I) or (III) are useful as medicinal agents in mammals, including humans, for the clinical and therapeutic treatment of diseases caused by various pathogenic microorganisms, especialy gram-negative bacteria. They are also useful as immunostimulants in mammals, including humans, having an increased risk of infection due to existing or clinically-induced immunosuppression.

The test procedure employs normal or immunocompromised $C_3H/HeN$ male mice from the Charles River Breeding Laboratory. The mice are acclimatized for 5 days before use and then treated either subcutaneously (SC) or orally (PO) with various dilutions (100, 10, 1 and 0.1 mg/kg) of the test compound or placebo (pyrogen free saline) using a volume of 0.2 ml. The treatment regiment was dependent on the infectious organism utilized: 24 and 0 hours before challenge for *Klebsiella pneumoniae* in normal mice; and 3, 2 and 1 day(s) before challenge for *Escherichia coli* or *Staph. aureus* in immunocompromised mice. The challenge is administered intramuscularly (IM) in the hip in the case of *K. pneumoniae* or intraperitoneally (IP) in the case of *E. coli* and *Staph. aureus*. A volume of 0.2 ml. was used for the challenge. Mortality was recorded after 7 days in the case of *K. pneumoniae* and after 3 days in the case of the other two microorganism challenges.

Culture Preparation:

*K. pneumoniae, E. coli,* or *Staph. aureus*: the culture was streaked for purity from frozen blood stock on brain heart infusion (BHI) agar. Three colonies were picked from the 18 hour plate culture and placed into 9 ml. of BHI broth. The broth culture was grown for 2 hours at 37° C. on a rotary shaker after which 0.2 ml. was streaked on the surface of several BHI agar slants. Following an 18 hour incubation at 37° C., the slants were washed with BHI broth, the culture density adjusted using a spectronic 20 and the appropriate dilution made to achieve an LD90 challenge level in normal mice.

When used as antiinfective or immunostimulant agents in humans, the compounds (I) or (III) of this invention are conveniently administered via the oral, subcutaneous, intramuscular, intravenous or intraperitoneal routes, generally in composition forms, which are standard in pharmaceutical practice. For example, they can be admnistered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg. of the active component are suitable for most applications.

The physician will determine the dosage which will be most suitable for an individual patient and it will vary with the age, weight and response of the particular patient and the route of administration. The favored oral dosage range is from about 1.0 to about 300 mg/kg/day, in simple or divided doses. The favored parenteral dose is from about 1.0 to about 100 mg/kg/day; the more favored range being from about 1.0 to about 20 mg/kg/day.

The following examples are given by way of illustration and are not to be construed as limitations of this invention, many variations of which are possible within the scope and spirit thereof.

EXAMPLE 1

R-trans-4-Hexen-3-ol

In a 500 ml. 3-necked round bottom flask equipped with a magnetic stirrer, septum, thermometer and $N_2$ inlet was placed 270 ml. $CH_2Cl_2$ and 7.2 g. of 4A type molecular seives. $Ti[OCH(CH_3)_2]_4$ (10.7 ml., 0.036 mol) was added via syringe and the mixture cooled to $-66°$ C., at which point L-(+)-diisopropyl tartrate (10.1 g., 0.043 mol), diluted with 10 ml. $CH_2Cl_2$ to reduce its visosity, was added by cannula and washed in with 5 ml. additional $CH_2Cl_2$. The temperature rose to $-62°$ C., at which point, racemic trans-2-hexen-4-ol (3.60 g., 0.036 mol) was added and washed in with 5 ml. $CH_2Cl_2$. After stirring in the acetone/dry ice bath for 8 minutes, the temperature fell to $-68°$ C., at which point t-butyl hydroperoxide (7.18 ml. of 3M in toluene, 0.022 mol) was added by syringe. The reaction mixture was warmed to $-35°$ C. and held for 18 hours at that temperature in a freezer. The cold mixture was then filtered, using fluted filter paper, into a stirred mixture of 540 ml. acetone and 11 ml. $H_2O$ which had been chilled to $-20°$ C. The mixture was slowly warmed to room temperature and stirred for 20 hours. The mixture was filtered over diatomaceous earth with $CH_2Cl_2$ wash. The combined filtrate and wash was stripped, without heat, to an oil (17.62 g.). Overstripping was avoided, since the desired product is quite volatile. The oil was chromatographed on 176 g. silica gel, using 4:1 hexane:isopropyl ether as eluant, monitoring by tlc. Solvent was removed by distillation using a short column packed with glass helices equipped with a variable takeoff head. Solvents, boiling to a head temperature of 69.5° C. (at which point head temperature began to fall) were thereby removed to leave substanitally pure, title product as a pot residue; tlc Rf 0.25 (3:1 hexane:ether). In a repeat of this experiment, more volatile 4:1 pentane:ether was employed as eluant, so as to expedite solvent removal and to minimize product loss on stripping.

EXAMPLE 2

Ethyl R-3-Methyl-4-hexenoate

The product of the preceding Example (0.4 g.), triethyl orthoacetate (3 ml.) and pivalic acid were heated at reflux for 2.5 hours, cooled and the entire reaction mixture twice chromatographed on silica gel, initially with 6:1 hexane:ether as eluant to yield 0.45 g. of product, and then with 7:1 hexane:ether as eluant to yield purified title product, 0.35 g.; ir (film) 2960, 1736, 1456, 1367, 1334, 1280, 1232, 1172, 1028, 962, 840 cm$^{-1}$.

Alternatively, pentane/ether column fractions containing the pure S-trans-2-hexen-4-ol were introduced directly in this step, with the pentane and ether initially distilled out of the reaction mixture.

Propionic acid was substituted for pivalic acid with substantially the same result. Dry HCl and 2,4-dinitrophenol were also successfully employed as the acid catalyst, but AlCl$_3$, as used in the next Example is the preferred catalyst.

EXAMPLE 3

R-3-Methyl-4-heptenoic Acid

Method A

In a 35 ml. flask, equipped with a magnetic stirrer and a Soxhlet extractor containing 4A-type molecular sieves in the thimble, was placed the product of the preceding Example (1.5 g., 0.015 mol). Triethyl orthoacetate (9 ml., 0.049 mol) and then AlCl$_3$ (0.12 g., 0.009 mol) were added, and the mixture refluxed over the Soxhlet extractor for 2 hours, by which time tlc indicated that conversion to intermediate ethyl R-3-methyl-4-hexenoate was complete; tlc Rf 0.75 (4:1 hexane:ethyl acetate, Rf 0.85 (15:5:2 hexane:ether:acetic acid).

The reaction mixture was cooled, diluted with 15 ml. 2N NaOH and 12 ml. of CH$_3$OH, and stirred for 27 hours at ambient temperature, by which time tlc indicated that hydrolysis was complete. The reaction mixture was stripped of methanol, diluted with 12 ml. H$_2$O and extracted 3×25 ml. CH$_2$Cl$_2$. The combined CHCl$_2$ were back washed 1×25 ml. 2N NaOH. The aqueous layer and back wash were combined, the pH adjusted to 1 with concentrated HCl, and extracted 3×CH$_2$Cl$_2$. The latter organic layers were combined, dried over MgSO$_4$ and stripped to yield title product as an oil, 1.28 g. (60%); tlc Rf 0.65 (15:5:2 hexane:ether:acetic acid); $^1$H-nmr (CDCl$_3$) delta (ppm) 9.4 (s, 1H), —CO$_2$H), 5.5 (m, 2H, —CH=CH—), 3.0-1.6 (m, 5H), 1.3-0.8 (m, 6H); ir (film) 3400-2400, 2960, 2925, 2860, 1708, 1458, 1410, 1380, 1295, 1228, 1190, 1152, 1100, 930 cm$^{-1}$.

Method B

Ester product of the preceding Example (0.24 g.) was combined with 25 ml. CH$_3$OH and 11.5 ml. 1N NaOH. The mixture was stirred 3.5 hours at ambient temperature, by which time tlc indicated that hydrolysis was complete. The mixture was extracted 2×35 ml. ether, adjusted to pH 2 with concentrated HCl and extracted 3×35 ml. ether. The acid extracts were combined, dried and stripped to yield title product, 0.20 g., identical with the product of Method A.

EXAMPLE 4

Ethyl S-3-Methylheptanoate

The product of Example 2 (0.20 g.) is hydrogenated in 40 ml. ethyl acetate over 0.20 g. of 5% Pd/C (50% water wet) under 4 atmospheres pressure of hydrogen in a Paar hydrogenation apparatus for 3 hours. Catalyst is recovered by filtration over diatomaceous earth. Title product is recovered by stripping the filtrate of solvent.

EXAMPLE 5

S-3-Methylheptanoic Acid

Method A

Product of Example 3 (0.20 g.) in 40 ml. ethyl acetate was hydrogenated over 0.2 g. of 5% Pd/C., 50% water wet, in a Paar hydrogenation apparatus under 4 atmospheres pressure of hydrogen for 3 hours. Catalyst was recovered by filtration over diatomaceous earth and title product recovered by stripping the filtrate to an oil, 0.2 g. If desired, purified title product is obtained by distillation under high vacuum; b.p. 77°–79° C./0.2 mm.; $^1$H-nmr (CDCl$_3$) delta (ppm): 12.0 (s, —COOH), 1.0 (d, —CH$_3$), 0.6-2.8 (m, remaining 13H); ir (film) 3400-2400, 2960, 2925, 2860, 1708, 1458, 1410, 1380, 1295, 1228, 1190, 1152, 1100, 930 cm$^{31\ 1}$; [alpha]$_D^{25}$ = −6.41°(=1% in CH$_3$OH); n$_D^{22.5}$ = 1.427.

Method B

Product of the preceding Example is hydrolyzed to title product according to Method B of Example 3.

EXAMPLE 6

S-3-Methylheptanoyl Chloride

The acid product of the preceding Example (8.5 g., 0.062 mol) was dissolved 18 ml. CH$_2$Cl$_2$. Oxalyl chloride (5.36 ml., 7.80 g., 0.0614 mol) was mixed into the solution and the mixture allowed to stand for 4 hours, by which time the reaction was complete, as evidenced by the lack of further gas evolution. This solution of acid chloride was immediately used directly in Example 8, Method C. Alternatively, the acid chloride was isolated by stripping away the solvent, for use in Method A of Example 8, and, if desired, was further purified by distillation, bp 45°/1.5 mm.

EXAMPLE 7

R-3-Methyl-4-heptenoyl Chloride

The acid product of Example 3 (0.747 g., 5 mmol) is converted to a CH$_2$Cl$_2$ solution of title product by the method of the preceding Example and used directly in Example 9 below. Alternatively the reaction mixture is stripped to yield title product, which, if desired, is distilled at reduced pressure.

EXAMPLE 8

N-(S-3-Methylheptanoyl)-D-gamma-glutamyl(alpha benzyl ester)-glycyl-D-alanine Benzyl Ester Method A To a solution of 1.0 g. (2.03 mmol) of D-gamma-glutamyl (alpha benzyl ester)-glycyl-D-alanine benzyl ester hydrochloride (Preparation 4) and 616 mg. (6.09 mmol) of triethylamine in 50 ml. of methylene chloride was added 660 mg. (4.06 mmol) of S-3-methylheptanoyl chloride and the reaction mixture stirred at room temperature for 80 hours. The methylene chloride was evaporated in vacuo and the residue dissolved in ethyl acetate. The resulting solution was washed sequentially with 2.5% hydrochloric acid, water, 10% potassium carbonate, water, and a brine solution. The organic phase was separated, dried over magnesium sulfate and concentrated under vacuum. The residue was triturated with diethyl ether and filtered under nitrogen to yield title product, all of which was used directly in Example 10, Method A.

Method B

The product of Preparation 4 (0.75 g., 1.53 mmol), 5 ml. CH$_2$Cl$_2$ and triethylamine (0.212 ml., 1.53 mmol) were combined and stirred under N$_2$. S-3-methylheptanoic acid (Example 5; 0.20 g., 1.39 mmol) in 4 ml. CH$_2$Cl$_2$ and then dicyclohexylcarbodiimide (0.286 g., 1.37 mmol) were added and the mixture stirred for 16 hours. The reaction mixture was filtered, the filtrate stripped, the residue taken up in 10 ml. ethyl acetate, and the solution washed in sequence with 5 ml. 2.5% HCl, 5 ml. H$_2$O, 5 ml. 10% K$_2$CO$_3$ and 5 ml. of brine, dried over MgSO$_4$ to yield 71 mg. (88%) of title product.

Method C

In a 500 ml. 4-necked round bottom flask equipped with stirrer, thermometer dropping funnel and N$_2$ inlet, the product of Preparation 4 (32.8 g., 0.059 mol) was dissolved in 175 ml. CH$_2$Cl$_2$ and cooled to 0°-5° C. Maintaining that temperature range, triethylamine (24.7 ml., 17.9 g., 0.177 mol, 3 equiv) was added as a slow stream over 15 minutes. The ice-water bath was maintained and the entire batch of S-3-methylheptanoyl chloride in CH$_2$Cl$_2$ from Example 6 added over 15 minutes as the temperature rose to 21° C. Stirring in the ice-water bath was continued for 45 minutes, by which time the gelatinous mixture became too thick to stir. The gelatinous mass was broken up and mixed with 125 ml. of 10% HCl and 50 ml. CH$_2$Cl$_2$. The organic layer was separated, washed sequentially 2×125 ml. H$_2$O, 2×125 ml. 10% K$_2$CO$_3$ and 1×125 ml. H$_2$O, dried over MgSO$_4$ and stripped to 82.3 g. of damp, white solids. These solids were taken up in 500 ml. of hot ethyl acetate. On slow cooling to ambient temperature, title product crystallized heavily, and the mixture was diluted with an additional 40 ml. ethyl acetate in order to maintain facile stirring. Purified title product was recovered by filtration and vacuum dried at 40° C., 31.1 g., (90.5%).

$^1$H-nmr (CDCl$_3$) delta (ppm): 8.4-8.1 (m, 3H), 7.15 (s, 10H), 5.1 (s, 4H), 4.4-4.2 (m, 2H), 3.7 (d, 2H), 2.2 (t, 2H), 2.1-1.7 (m, 6H), 1.4-1.1 (m, 10H), 0.92-0.8 (m, 6H).

EXAMPLE 9

N-(R-3-Methyl-4-heptenoyl)-D-gamma-glutamyl-(alpha benzyl ester)-glycyl-D-alanine Benzyl Ester By Method C of the preceding Example, the product of Preparation 4 (2.77 g., 5 mmol) is coupled with the entire batch of acid chloride in CH$_2$Cl$_2$ from Example 7. The product is recovered by stripping the washed and dried organic layer, and repeatedly dissolving the residue in ethyl acetate and restripping.

EXAMPLE 10

N-(S-3-Methylheptanoyl)-D-gamma-glutamyl-glycyl-D-alanine

Method A

The entire product of Method A of Example 8 was dissolved in 65 ml. of methanol. Palladium hydroxide (250 mg.) was added to the solution and the mixture shaken in a hydrogen atmosphere at 4 atmospheres pressure for 3 hours. The catalyst was filtered and the solvent removed in vacuo. The residue was dissolved in water and lyophilized to give desired product.

The NMR spectrum (DMSO-d$_6$) showed absorption at 8.27-8.03 (m, 3H), 4.32-4.1 (m, 2H), 3.72 (d, J=6Hz, 2H), 2.22 (t, J=8Hz, 2H), 2.27-1.68 (m, 6H), 1.42-1.0 (m, 10H) and 0.94-0.8 (m, 6H).

When carried out on a weighed quantity of the title product of Example 8 (0.50 g.), using 90 mg. of 20% Pd(OH)$_2$/C (31% water wet), in 25 ml. CH$_3$OH, this method gave 0.24 g. of the same, fluffy, electrostatic title product; ir (nujol mull) 3300, 2940, 1740, 1650, 1540, 1468 and 1380 cm$^{-1}$; all but the last two peaks are broad and poorly resolved.

Method B

The product of Method C of Example 8 (30.8 g.) was slurried in 300 ml. absolute ethanol in a 2 liter autoclave. 5% Pd/C 1.54 g., 50% water wet) was added and the mixture hydrogenated at 4× atmospheric pressure for 1 hour, by which time uptake of hydrogen was complete. The catalyst was recovered by filtration, first over paper, then over 0.45 micron nylon milipore, employing 100-150 ml. ethanol for transfer and wash. The combined filtrate and wash liquors were stripped to a damp, white solid, which was dissolved in a 150 ml. of a hot, 1:10 mixture of absolute ethanol and acetonitrile, clarified by hot filtration, boiled down to 35 ml., and slowly cooled to room temperature, granulated and filtered to yield crystalline, dense, non-electrostatic title product, 20.1 g. (94%) characterized by its ir (nujol mull) which includes major, well-resolved, sharp peaks at 3340, 3300, 2900, 2836, 1725, 1650, 1628, 1580, 1532, 1455, 1410, 1370, 1280, 1240, 1216 and 1175 cm$^{-1}$.

Method C

Crystalline product (9.4 g.), prepared according to immediately preceding Method B, was dissolved in 1000 ml. of acetone by heating at reflux for 1 hour. The solution was cooled to room temperature and seeded with a trace of Method B product to induce crystallization. After stirring for 6 hours, further purified title product was recovered by filtration, with minimal acetone wash, and dried in vacuo at 35° C., 7.25 g., having identical ir peaks to those of the acetonitrile/ethanol crystals of Method B.

Method D

The product of the preceding Example (0.50 g.) was combined with 0.026 g. of 5% Pd/C (50% water wet) in 125 ml. of absolute ethanol in a Paar hydrogenation bottle. The mixture was hydrogenated under 4× atmospheric pressure of hydrogen for 2.5 hours. Catalyst was recovered by filtration and the filtrate stripped to yield title product as tackey solids which are crystalized according to the immediately preceding Methods.

EXAMPLE 11

N-(R-3-Methyl-4-heptenoyl)-D-gamma-glutamyl-glycyl-D-alanine

The product of Example 9 (1 g.) is dissolved in 5 ml. CH$_3$OH. 1N NaOH (2.50 ml.) is added and the mixture stirred 3 hours at ambient temperature. The CH$_3$OH is stripped and the aqueous residue diluted with 7.5 ml. H$_2$O, extracted 2×7.5 ml. ethyl acetate, and acidified to pH 3.0 with 1N HCl. The acidified aqueous is extracted continuously with fresh ethyl acetate, and the extract stripped to yield title product which is converted to a lyophilate according to Method A of Example 10.

EXAMPLE 12

R-trans-4-Hepten-3-ol

By the method of Example 1, but using a reaction temperature of −20° C. at all stages during combination of the reagents, the title product of Preparation 5 (10 g., 0.088 mol) was converted to present title product. After all the reagents were combined, the mixture was stirred 1.5 hours at −20° C., then warmed to room temperature, quenched by dropwise addition of 25 ml. H$_2$O and then 6 ml. 30% NaOH (saturated with NaCl). The quenched mixture was stirred for 20 minutes, diluted with 30 ml. CH$_2$Cl$_2$ and the aqueous layer separated and washed 2×50 ml. fresh CH$_2$Cl$_2$. The organic layers were combined, dried over MgSO$_4$ and distilled to a residual volume of 50 ml., which was chromatographed on silica gel using pentane and then 4:1 pentane:ether as eluant. Initial fractions containing a less polar impurity were discarded. Pure product fractions, having Rf 0.3 (4:1 pentane:ether), were combined and stripped to yield title product as a clear, colorless liquid, 5.7 g.

EXAMPLE 13

R-3-Ethyl-4-heptenoic Acid

By Method A of Example 3, except to use ether in place of CH$_2$Cl$_2$ in isolation, the product of the preceding Example (5.7 g., 0.05 mol) was condensed with ethyl orthoacetate, rearranged and saponified to yield present title product as an oil, 1.4 g.; tlc Rf 0.4 (2:1 hexane:ether). The intermediate ethyl ester showed Rf 0.25 in the same tlc system.

EXAMPLE 14

S-3-Ethylheptanoic Acid

The product of the preceding Example (1.4 g.) was hydrogenated in 20 ml. CH$_3$OH over 0.1 g. 5% Pd(OH)$_2$/C at 4× atmospheric pressure for 1 hour. Catalyst was recovered by filtration. The filtrate was stripped of solvent and the residue distilled to yield title product, 1.0 g.; bp 76°-77° C./0.4 torr; [alpha]$_D^{25}$ −1.6°(C=2% in CH$_3$OH).

EXAMPLE 15

S-3-Ethylheptanoyl Chloride

Under dry N$_2$, the product of the preceding Example (1.0 g., 0.00633 mol) was dissolved in 10 ml. CH$_2$Cl$_2$. Oxalyl chloride (0.547 ml., 0.00627 mol) was added and the mixture stirred for 1 hour, by which time evolution of gas had ceased. The resulting solution of title product was evaporated under a stream of N$_2$ to 7 ml. and used directly in the next step.

By the same method, the unsaturated acid of Example 13 is converted to a solution of R-3-ethyl-4-heptenoyl chloride.

EXAMPLE 16

N-(S-3-Ethylheptanoyl)-D-gamma-glutamyl (alpha benzyl ester)-glycyl-D-alanine Benzyl Ester The title product of Preparation 4 (1.1 g., 0.00222 mol) was dissolved in 30 ml. CH$_2$Cl$_2$ and triethylamine (0.935 ml., 0.00666 mol). The CH$_2$Cl$_2$ solution of S-3-ethylheptanoyl chloride (2.3 ml., 0.00211 mol) of the preceding Example was added and the mixture stirred under N$_2$ for 0.75 hour, washed sequentially with 20 ml. portion of 10% HCl, H$_2$O, 10% K$_2$CO$_3$ and saturated brine, dried over MgSO$_4$, stripped to a solid residue, triturated with ether and recovered by filtration, 0.8 g. The latter was taken up in ethyl acetate, rewashed as above and restripped to a second solid, 0.7 g., which was chromatographed on silica gel using 97:3 CHCl$_3$:CH$_3$OH as eluant to yield purified title product, 467 mg.

By the same method, 3-ethyl-4-heptenoyl chloride is coupled with the title product of Preparation 4 to yield N-(R-3-ethyl-4-heptenoyl)-D-gamma-glutamyl (alpha benzyl ester)-glycyl-D-alanine benzyl ester.

EXAMPLE 17

N-(S-3-Ethylheptanoyl)-D-gamma-glutamyl-glycyl-D-alanine

The title product of the preceding Example (467 mg.) was hydrogenated by the method of Example 14. After recovery of the catalyst, the filtrate was stripped to a foam, taken up in H$_2$O, filtered and lyophilized to yield title product, 238 mg.

$^1$H-nmr (DMSO-d$_6$) delta (ppm): 8.20-8.00 (m, 3H), 4.24-4.16 (m, 2H), 3.74-3.60 (m, 2H), 2.18 (t, J=7, 2H), 2.02 (d, J=7, 2H), 2.02-1.60 (m, 3H), 1.26 (d, J=6, 3H), 1.26-1.08 (m, 8H), 0.92-0.74 (m, 6H).

By the same method the unsaturated product of the preceding Example is converted to the same product.

EXAMPLE 18

N-(R-3-Ethyl-4-heptenoyl)-D-gamma-glutamyl-glycyl-D-alanine

The unsaturated product of Example 16 is hydrolyzed to present title product by the method of Example 11.

EXAMPLE 19

N-(S-3-Ethylheptanoyl)-D-gamma-glutamyl (alpha benzyl ester)-glycyl-D-alanine Butyl Ester By the methods of Example 17, S-3-ethylheptanoyl chloride of Example 16 and D-gamma-glutamyl (alpha benzyl ester)-glycyl-D-alanine butyl ester (1.0 g., 0.00222 mol) coupled to produce present title product, isolated and purified in like manner. The yield was 0.7 g.

$^1$N-nmr (DMSO-d$_6$) delta (ppm): 8.22 (d, J=7, 1H), 8.12-8.00 (m, 2H), 4.40-4.16 (m, 2H), 4.08-3.95 (m, 2H), 3.75-3.62 (m, 2H), 2.18 (t, J=6, 2H), 2.02 (d, J=6, 2H), 2.04-1.62 (m, 3H), 1.60-1.46 (m, 2H), 1.38-1.10 (m, 15H), 0.90-0.75 (m, 9H).

By the same method R-3-ethyl-4-heptenoyl chloride is converted to N-(R-3-ethyl-4-heptenoyl)-D-gamma-glutamyl (alpha benzyl ester)-glycyl-D-alanine butyl ester.

EXAMPLE 20

N-(S-3-Ethylheptanoyl)-D-gamma-glutamyl-glycyl-D-alanine Butyl Ester

By the method of Example 14, the title product of the preceding Example was hydrogenated to produce present title product. Following recovery of the catalyst, the filtrate was stripped to solids which were recovered by trituration with ether and filtration, 256 mg., mp 130°-131° C.

By the same method, the unsaturated product of the preceding Example is converted to the same product.

EXAMPLE 21

R-3-Ethyl-4-heptenal

A solution of R-trans-4-hepten-3-ol of Example 12 (3.0 g.) in 300 ml. of dry ethyl vinyl ether is heated at reflux while a series of five $Hg(OAc)_2$ additions (2 g. each, at two hour intervals) is made. After an additional 18 hours at reflux, the clear solution is cooled to room temperature, treated with 0.5 ml. of glacial acetic acid, and stirred for three hours. The resulting solution is diluted with ether, poured into 200 ml. of 5% KOH solution, and extracted three times with ether. The combined ether extracts are then dried over $K_2CO_3$ and stripped to yield the allyl vinyl ether, R-trans-O-vinyl-4-hepten-3-ol.

A solution of said allyl vinyl ether (2.3 g.) in 20 ml. of decalin is refluxed for 10.5 hours. The resulting solution is then cooled to room temperature and placed directly on a column of silica gel. Following hexane flush to remove the decalin, title is recovered by elution of the column with ether and stripping.

EXAMPLE 22

S-3-Ethyl-4-heptenoic Acid

The product of the preceding Example (100 mg.) is dissolved in 4 ml. of acetone and cooled to 0°-5° C. In a separate flask, $CrO_3$ (72.1 g., 0.72 mol) was mixed with 50 ml. $H_2O$ and stirred at 0°-5° C. and 62.1 ml. concentrated $H_2SO_4$ slowly added, and the mixture diluted to 250 ml. with $H_2O$ to yield a 2.88M solution of $H_2CrO_4$ (Jones reagent). The latter solution (1 ml.) is added portionwise to the above acetone solution over 1 hour. The temperature rises and is maintained at 17°-25° C. as the reagent is added. The mixture is recooled to 6° C., 70 ml. of 2-propanol added over 10 minutes (during which the temperature is allowed to rise to 20° C.), and then concentrated in vacuo to an oil to which is added with stirring 8 ml. of 2.5N NaOH over 50 minutes, maintaining temperature 22±5° C. The mixture is heated and filtered over diatomaceous earth with hot 2.5N NaOH wash. The combined filtrate and wash are extracted 3×300 ml. isopropyl ether. The combined organic layers are back extracted with 200 ml. 2N NaOH. The combined aqueous layers are acidified to pH 1.0 by the slow addition of 0.5 ml. concentrated HCl and product extracted into 3×300 ml. fresh isopropyl ether. The organic extracts are combined and stripped to yield title product as an oil.

PREPARATION 1

Racemic trans-4-Hexen-3-ol

In a 3 liter 4-necked flask equipped with stirrer, addition funnel, thermometer and nitrogen inlet was placed 400 ml. THF. The THF was cooled to −70° C. and ethylmagnesium bromide (600 ml. of 2M in THF, 1.2 mol) added. Maintaining the temperature −70° to −60° C., crotonaldehyde (78 ml., 0.94 mol) was added over 7 minutes. After stirring for 20 minutes at −70° C., then for 1 hour as the mixture gradually warmed to −20° C., the mixture was recooled to −70° C. and carefully quenched with 200 ml. of saturated $NH_4Cl$ (initial foaming), warmed to ambient temperature and diluted with 200 ml. $CH_3COOH$ and 100 ml. $H_2O$. The two layer system was saturated with NaCl. The aqueous layer was separated and extracted 2×500 ml. ether. The original organic layer and ether extracts were combined, washed 4×250 ml. saturated $NaHCO_3$, dried over $MgSO_4$, stripped and the residue distilled at atmospheric pressure, 69 g.; b.p. 133°-137° C., $^1$H-nmr ($CDCl_3$) delta (ppm): 5.53 (complex m, 2H), 3.93 (m, 1H), 2.26 (s, 1H), 1.71 (d, 3H), 1.43 (m, 2H), 0.84 (t, 3H).

PREPARATION 2

Glycyl-D-alanine benzyl ester hydrochloride

To a cold (0° C.) solution of 100 ml. methylene chloride containing 10 g. (57 mmol) of N-t-butyloxy-carbonylglycine, 20 g. (57 mmol) of D-alanine benzyl ester p-toluene sulfonic acid salt and 5.77 g. (57 mmol) of triethylamine was added 12.3 g. (60 mmol) of dicyclohexylcarbodiimide and the resulting reaction mixture allowed to warm to room temperature. After 18 hours the mixture was filtered and the filtrate concentrated in vacuo. The residue was dissolved in 200 ml. of ethyl acetate and the organic layer washed with 2.5% hydrochloric acid, water, a saturated sodium bicarbonate solution and a brine solution. The organic layer was separated, dried over magnesium sulfate and evaporated under reduced pressure. To the resulting oil 200 ml. of dioxane saturated with hydrogen chloride was added. After 30 minutes 400 ml. of diethyl ether was added and the product filtered under nitrogen, 10.9 g. (70% yield).

PREPARATION 3

N-t-Butoxycarbonyl-D-gamma-glutamyl (alpha benzyl ester)hydrosuccinamide ester To 1500 ml. of methylene chloride containing 50 g. (143 mmol) of N-t-butoxycarbonyl-D-gamma-glutamic acid alpha-benzyl ester and 17.3 g. (150 mmol) of N-hydroxy-succinamide was added 30.9 g. (15 mmol) of dicyclohexylcarbodiimide and the resulting reaction mixture allowed to stir at room temperature for 18 hours. The solids were filtered and the filtrate concentrated in vacuo. The residue was triturated with diethyl ether and the solids filtered under nitrogen, 43.7 g. (68% yield).

PREPARATION 4

D-gamma-Glutamyl (alpha benzyl ester)-glycyl-D-alanine benzyl ester hydrochloride A solution containing 4.3 g. (9.45 mmol) of N-t-butoxycarbonyl-D-gamma-glutamyl (alpha benzyl ester) hydroxysuccinamide ester, 2.71 g. (9.92 mmol) of glycyl-D-alanine benzyl ester hydrochloride and 1.0 g. (9.92 mmol) of triethylamine in 100 ml. of methylene chloride was allowed to stir at room temperature for 18 hours, and was then concentrated in vacuo. The residue was dissolved in 200 ml. of ethyl acetate and the solution washed with 2.5% hydrochloric acid, water, 10% potassium carbonate and a brine solution. The organic phase was separated, dried over magnesium sulfate and evaporated under reduced pressure. The residue was treated with 200 ml. of dioxane saturated with hydrogen chloride and allowed to stir for 2 hours. The solution was concentrated to dryness in vacuo and the residue triturated with diethyl ether. The solids were filtered under nitrogen, 3.41 g. (73% yield).

By the same method, the product of the preceding Preparation and glycyl-D-alanine butyl ester were converted to D-gamma-glutamyl (alpha benzyl ester)-glycyl-D-alanine butyl ester.

PREPARATION 5

Racemic trans-4-Heptene-3-ol

By the method of Preparation 1, except to use ordinary ether as solvent, 2-pentenal (25 g., 0.30 mol) was converted to distilled title product, 25.6 g.; b.p. 145°–150° C.

What is claimed is:

1. A process for the synthesis of a compound of the absolute stereochemical formula

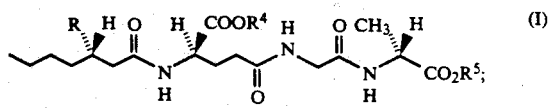

wherein R is methyl or ethyl, and $R^4$ and $R^5$ are each hydrogen, or one of $R^4$ and $R^5$ is hydrogen and the other is $(C_1-C_6)$alkyl or $(C_6-C_8)$cycloalkylmethyl, which comprises the steps of (a) coupling an activated form of R-trans-3-methyl-4-heptenoic acid or R-trans-3-ethyl-4-heptenoic with a compound of the absolute stereochemical formula

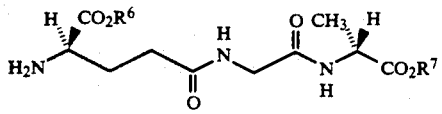

wherein $R^6$ and $R^7$ are each benzyl, or one of $R^6$ and $R^7$ is benzyl and the other is $(C_1-C_6)$alkyl or $(C_6-C_8)$cycloalkylmethyl to form a compound of the absolute stereochemical formula

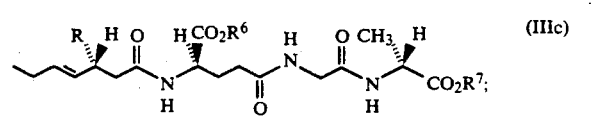

and (b) hydrogenation of the compound of the formula (IIIc) to form the compound of the formula (I) with concurrent reduction of the double bond and hydrogenolysis of benzyl ester group(s).

2. A process of claim 1 wherein the activated form of the acid is R-trans-3-methyl-4-heptenoyl chloride, R is methyl, $R^6$ and $R^7$ are both benzyl and $R^4$ and $R^5$ are both hydrogen.

3. A process of claim 1 wherein the activated form of the acid is R-trans-3-ethyl-4-heptenoyl chloride, R is ethyl, $R^6$ and $R^7$ are both benzyl and $R^4$ and $R^5$ are both hydrogen.

4. A compound of the formula

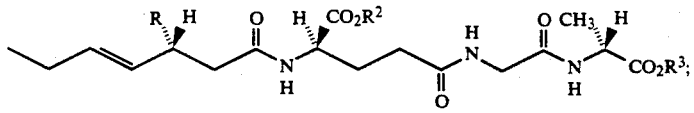

wherein R is methyl or ethyl; and $R^2$ and $R^3$ are each hydrogen, or $R^2$ and $R^3$ are each independently $(C_1-C_6)$alkyl, $(C_6-C_8)$cycloalkylmethyl or benzyl; or a pharmaceutically acceptable cationic salt thereof when $R^2$ and $R^3$ are hydrogen.

5. The compound of claim 4 wherein R is methyl and $R^2$ and $R^3$ are each hydrogen.

6. The compound of claim 4 wherein R is methyl and $R^2$ and $R^3$ are each benzyl.

7. The compound of claim 4 wherein R is ethyl and $R^2$ and $R^3$ are each hydrogen.

8. The compound of claim 4 wherein R is ethyl, $R^2$ is benzyl and $R^3$ is butyl.

* * * * *